United States Patent [19]

Duränzampa et al.

[11] Patent Number: 5,034,002
[45] Date of Patent: Jul. 23, 1991

[54] AUTO-NON-REUSABLE SYRINGE-NEEDLE SYSTEM FOR INJECTIONS FOR A UNIQUE USE

[75] Inventors: Ricardo A. Duränzampa; Ruben Maier, both of Cordoba, Argentina

[73] Assignee: Fabersanitas S.A., Spain

[21] Appl. No.: 547,688

[22] Filed: Jul. 2, 1990

[30] Foreign Application Priority Data

Jul. 3, 1989 [AR] Argentina ............................ 314315

[51] Int. Cl.$^5$ ................................................ A61M 5/00
[52] U.S. Cl. ...................................... 604/110; 604/218
[58] Field of Search ........................ 604/110, 187, 218

[56] References Cited

U.S. PATENT DOCUMENTS 4,233,975  11/1980  Yerman ............................... 604/110
4,391,272   7/1983  Staempfli ........................... 604/110

FOREIGN PATENT DOCUMENTS 0321414  6/1989  European Pat. Off. ............ 604/110
89/03628  5/1989  World Int. Prop. O. .......... 604/110

Primary Examiner—John D. Yasko
Attorney, Agent, or Firm—Ostrolenk, Faber, Gerb & Soffen

[57] ABSTRACT

Auto-non-reusable syringe-needle system for injections, for a single use, composed of a barrel (1) to contain the liquid to be injected, a piston (2) impelled by a plunger (3) to make it slide through the inside of the barrel (1), an internal rib or emergence (5) in the form of a ring and which emerges from the syringe-needle body between the front side of the completely introduced piston (2) and the tip of the canula (4) opposite to the bevel, which forms two fixed seats (6 and 7) on both of the valve for a moving body (8) located in the interior and coaxially movable and which has an elastic flexible circular emergence (9) which can act on the two seats (6 and 7) and which can go from a position whereby it allows movement in the direction of suction of the liquid, to a direction of injection, said moving body (8) having emergences (10) which serve as guides and which have channels (10) for the passage of the liquid.

3 Claims, 6 Drawing Sheets

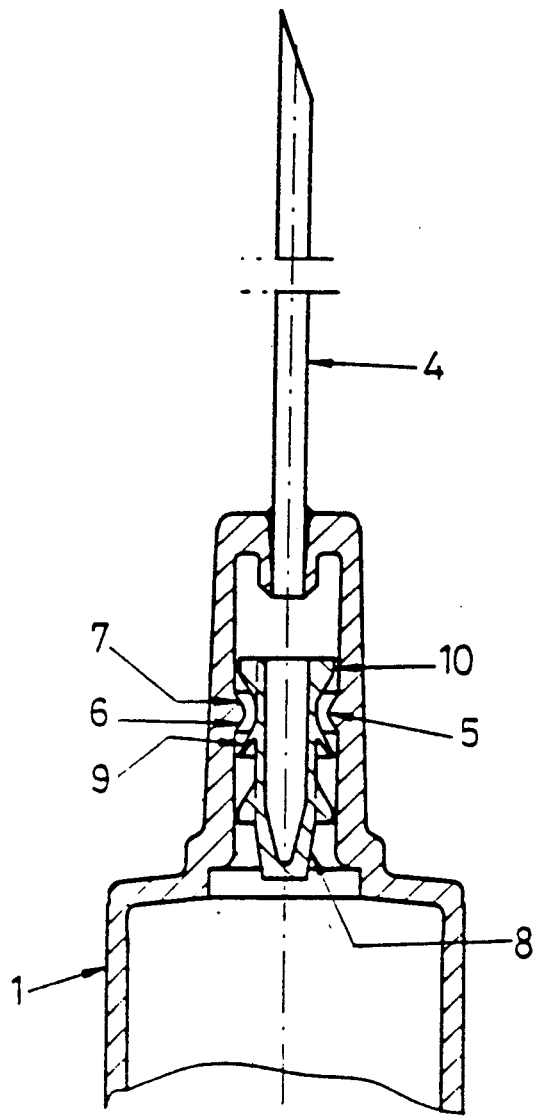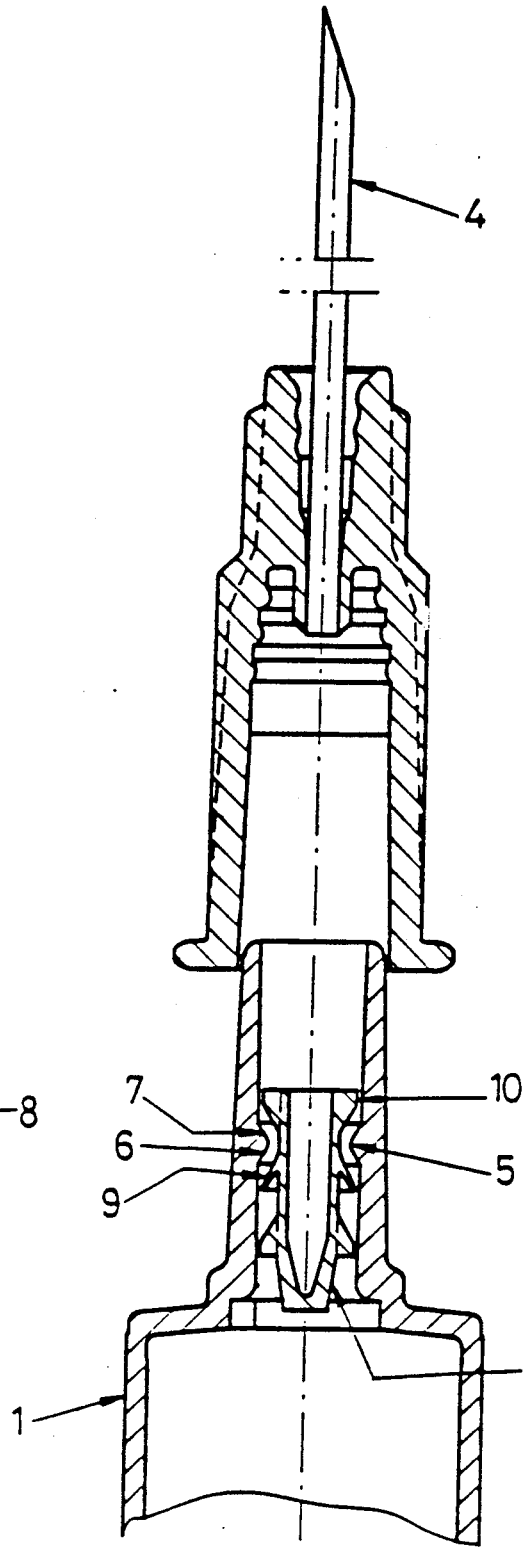
FIG. 7
FIG. 8

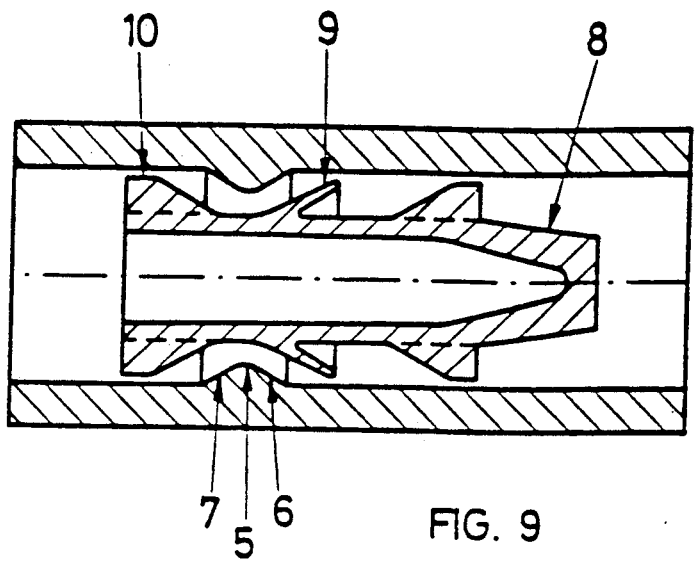
FIG. 9
FIG. 10
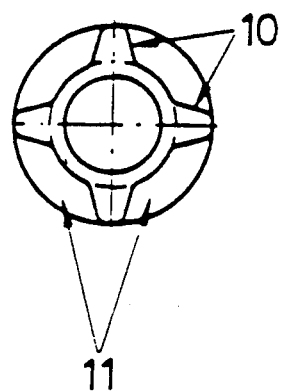

AUTO-NON-REUSABLE SYRINGE-NEEDLE SYSTEM FOR INJECTIONS FOR A UNIQUE USE

The object of the presents invention is a system of auto-non-reusable syringe-needle for injections, that is to say, that can have only one and unique use, independently of the user's wish.

The known syringes for single use carry out the function of injecting any fluid and are discarded. But they have the great inconvenient of being unduly reused, with the subsequent risk of germ transmission, which can only be avoided if they are discarded after their first and unique use.

We subsequently propose a system that avoids the reuse of the mentioned syringe-needle system, independently of the user's wish.

This system is based on a valve that allows the suction and filling of the syringe, as well as the injection or emptying, changing the valve's position in this last phase, in such a way that when it is tried to be reused, it blocks the fluid passage, avoiding thus the refilling of the syringe.

For better comprehension we attach some figures, where several examples of realization are illustrated, for showing but not limiting some of the many possible variants from the same inventive concept.

FIGS. 7, 8 and 9 also show views in longitudinal cut of another realization variant of the valve situated in different places of the ejection part. FIG. 9 illustrates a complete valve set situated in any area of the ejection part of the mentioned syringe-needle system. FIG. 10 shows a frontal view of the mobile element of the valve represented in FIGS. 7, 8 and 9.

Figure 1:
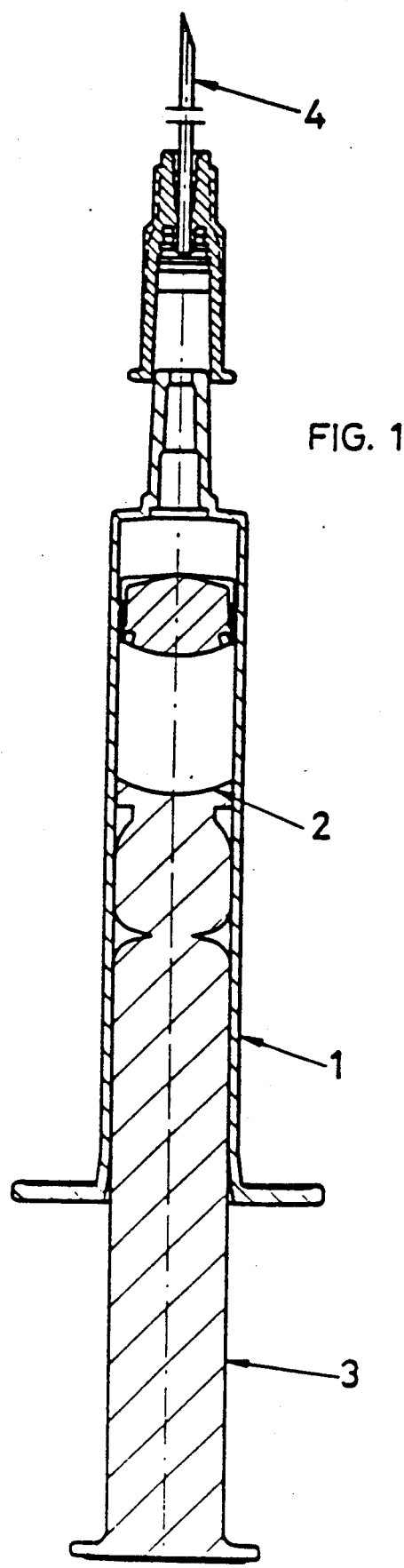
FIG. 1 is a view of the longitudinal cut of the syringe object of this invention.
Figure 2:
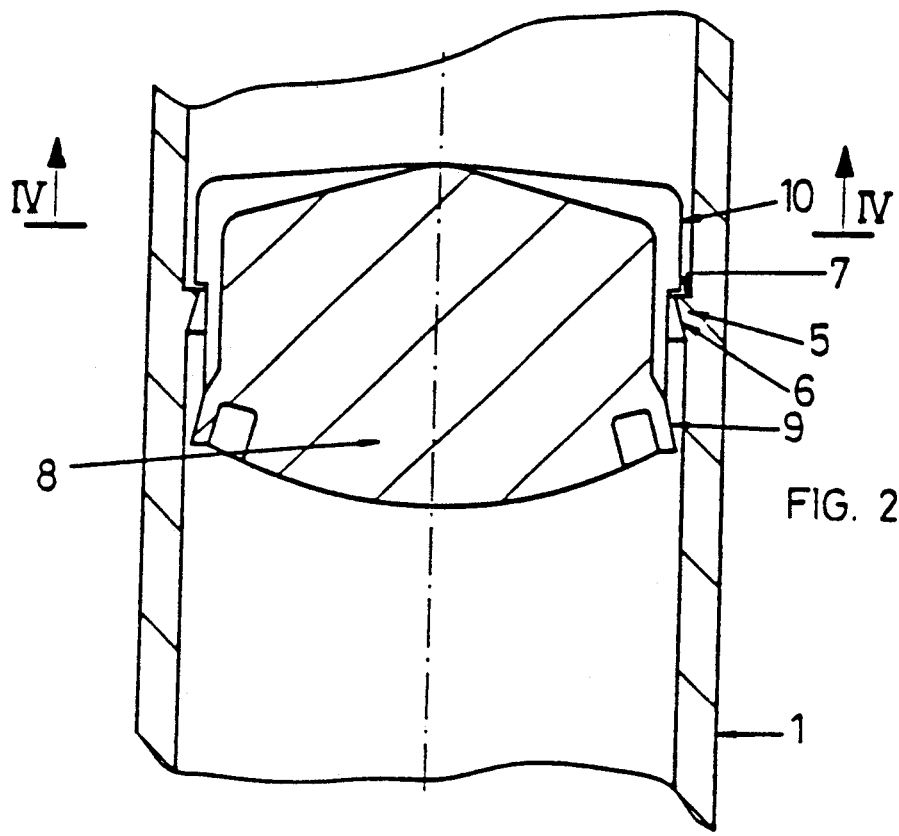
FIG. 2 is an enlarged view of the valve in longitudinal cut, placed in the syringe shown in FIG. 1, in the position of suction moment. This valve carries out the function of making the syringe unusable after its first use.
Figure 3:
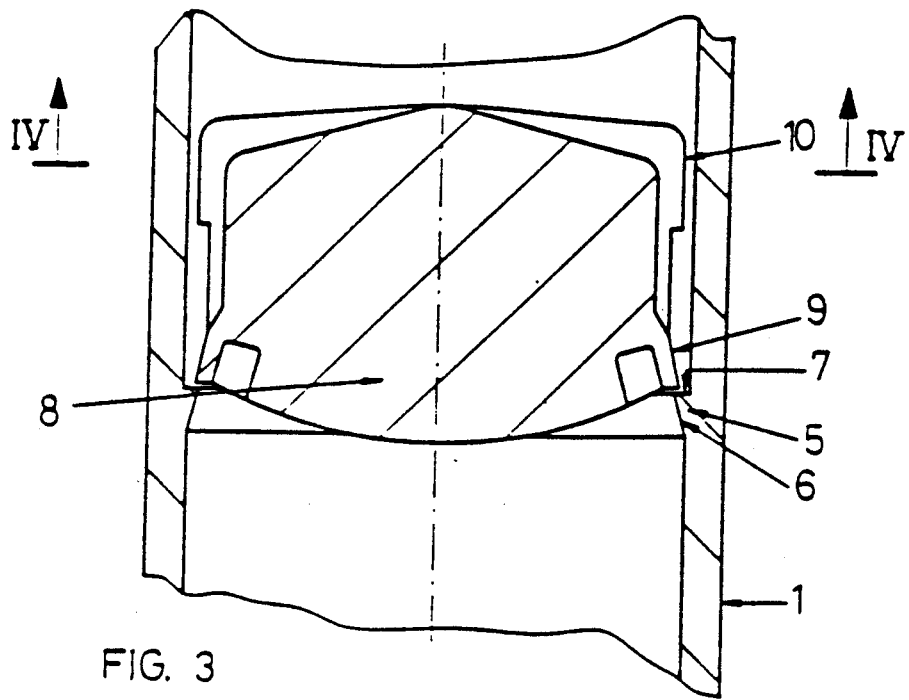
FIG. 3 shows a similar view to the latter in the position it is placed in the moment when injection starts and where it continues after injection.
Figure 4:
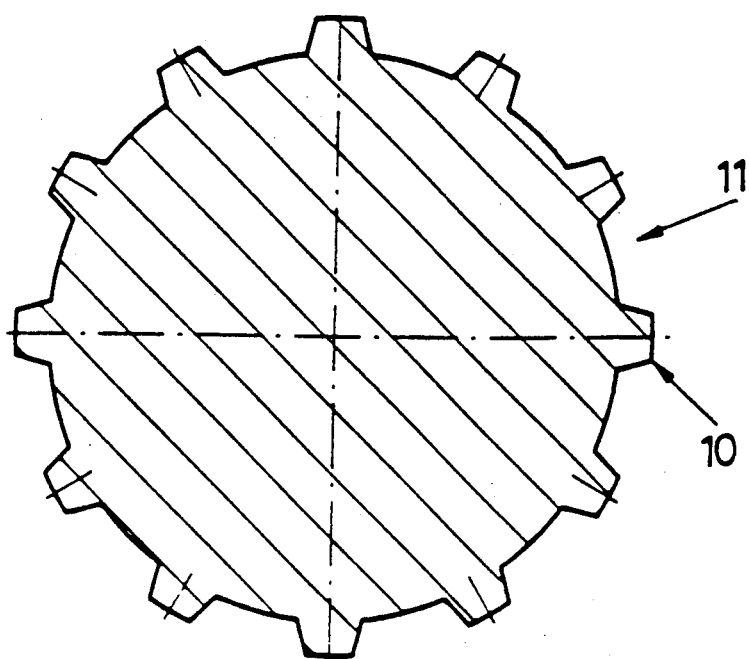
FIG. 4 shows a cut as per cutting line IV—IV of FIG. 2.
Figure 5:
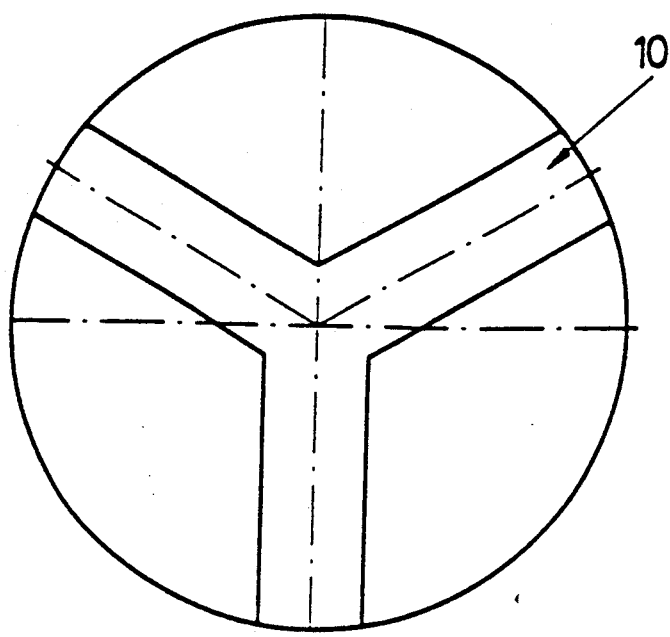
FIG. 5 shows a frontal view of the mobile valve, corresponding to one of the realization variants.
Figure 6:
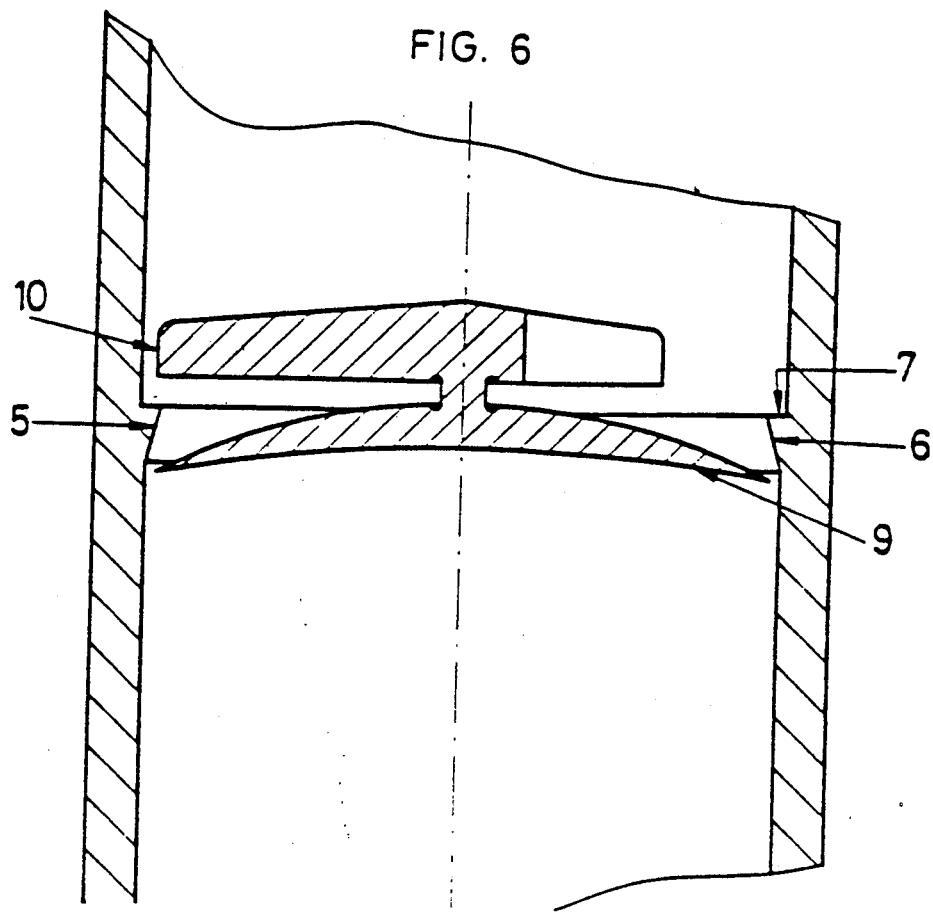
FIG. 6 shows the same variant of FIG. 5 in longitudinal cut, inside the cavity where it is placed.

With reference to all figures in general, and to FIGS. 1 to 4 in particular, we can see the auto-non-reusable syringe of the invention, formed by a barrel to contain the fluid (1) in which a piston slides (2) impelled by a plunger hand operated (3). All the above mentioned elements are known and usual in syringes for single use.

The ejecting part of the syringe-needle system located between the extreme position of the totally introduced piston (2) and the tip of the cannula (4) opposite to the bevel, has an emergent-ring of the inner surface, that forms at least two valve seats (6) and (7).

Coaxially arranged and surrounded by the said emergent ring-shaped seats it is placed the mobile element (8) of the valve formed by a body of revolution axially mobile due to the depression and pression of the fluid caused by the piston (2) when aspiration and injection of the said fluid happen respectively, having the mentioned body of revolution, in its back part, of the side of the piston (2), a circular emergent edge (9), substantially elastic and flexible, that forms two mobile seats of the valve in both sides and a plurality of ledges or ribs (10) in its front area, peripherally arranged, forming a plurality of grooves (11) that allow the entrance of the fluid when the plurality of ledges (10) reach the front part of the seat (7) of the ring (5) during the aspiration process of the syringe as well as when the mobile element (8) reaches the end of its run during the injection process. Being the position of the mobile element (8) before starting its use such that the mentioned ring (5) is placed between the elastic edge (9) and the plurality of ledge (10).

During the aspiration, the mobile element (8) moves backwards until the plurality of ledges (10) reach the ring (5) which avoids that the mobile element (8) is drawn by the fluid out of ejection part of the barrel at the same time that the fluid itself goes through the plurality of grooves (11). During the injection process, when it is started, the mobile body of the valve (8) is drawn by the fluid current until the front part of the elastic edge (9) reaches the back part of seat (6) of the ring (5), stopping the pass of the fluid making the mentioned edge (9) flex and compress through the increase in pressure of the liquid on the valve until the ring (5) is surpassed; avoiding from that moment on the reuse of the syringe because, if it is tried to be reused, when aspiring the fluid, the mobile body of the valve (8) moves backwards until the back part of the edge (9) reaches the front part of the ring (5), forming a tight closure and avoiding the refilling of the syringe, getting in this way the aim pursued.

What is claimed is:

1. Auto-non-reusable syringe-needle system for injection, for a unique use, formed by a barrel to contain the fluid to be injected, in which a piston impelled by a plunger slides, generally hand operated; characterized because in the inner surface of the ejecting part of the barrel of the syringe-needle system, located between the front side of the completely introduced piston and the tip of the cannula opposite to the bevel, there is an emergent ring that forms two fixed seats in both sides of the valve and coaxially arranged and surrounded by the said ring there is a mobile body of the valve formed by a revolution body axially mobile by the depression and pression of the fluid transmitted by the piston during the moments of aspiration and injection of the said fluid respectively, having the mentioned revolution body of the valve, in its back part —of the piston side—an emergent circular edge, substantially elastic and flexible, forming two mobile seats of the valve in both sides and a plurality of peripheral ledges in its front part alternate with a plurality of grooves that allow the entrance of the fluid when the plurality of ledges reach the front part of the ring during the syringe aspiration process, as well as when the mobile body of the valve reaches the end of its run during the injection process, being the position of the body of the valve before starting its use such that the mentioned ring is placed between the elastic edge and the plurality of ledges; during aspiration, the mobile body of the valve moves backwards until the plurality of ledges reach the ring, which avoids that the mobile body of the valve is drawn by the fluid into the barrel at the same that the fluid itself goes through the plurality of grooves; during the injection process, when it starts, the mobile body of the valve is moved by the current of the fluid until the front part of the elastic edge reaches the back part of the ring, thus avoiding the pass of the fluid and the increase of pressure makes the circular edge flex and compress until the ring is surpassed, thus allowing the pass of the fluid and avoiding from that moment on the reuse of the syringe because, when it is tried to be reused, when the fluid is aspired, the mobile body of the valve moves backwards until the back part of the edge reaches the front part of the ring, forming a tight closure and avoiding the syringe refilling, getting in this way the aim pursued.

2. Syringe-needle system, as per claim 1, characterized because the fix and mobile elements of the valve can form an independent set to be assembled in the ejecting area of the barrel of the syringe-needle system.

3. Syringe-needle system as per claim 1, characterized because the back part of the revolution body that forms the mobile body of the valve extends the emergent circular edge, having a plurality of ledges in its extension of a minor outer diameter than the inner diameter of the surface of the ejecting part where it is placed, but of larger diameter than the inner diameter of the ring, alternate with a plurality of grooves that allow the entrance of the fluid.

* * * * *